United States Patent [19]

Kumar

[11] 4,196,056
[45] Apr. 1, 1980

[54] ION SELECTIVE ELECTRODE ANALYSIS

[75] Inventor: Anand Kumar, Monroe, N.Y.

[73] Assignee: Technicon Instruments Corporation, Tarrytown, N.Y.

[21] Appl. No.: 956,006

[22] Filed: Oct. 30, 1978

[51] Int. Cl.$^2$ ............................................. B01D 59/40
[52] U.S. Cl. ............................... 204/1 T; 204/195 M; 260/429 J
[58] Field of Search .................. 204/1 B, 195 M, 1 T; 260/429 J

[56] References Cited

U.S. PATENT DOCUMENTS

| | | | |
|---|---|---|---|
| 3,406,102 | 10/1968 | Frant et al. | 204/1 T |
| 3,483,112 | 12/1969 | Ross | 204/1 T X |
| 3,894,917 | 7/1975 | Riseman et al. | 204/1 B |

OTHER PUBLICATIONS

Komutsu et al., Nippon Kagaku Zasshi, 88 (1), pp. 63–66, (1967).
Nomura, Nippon Kagaku Zasshi, 88 (2), pp. 199–202, (1967).

*Primary Examiner*—Helen M. S. Sneed
*Attorney, Agent, or Firm*—S. P. Tedesco; Robert S. Salzman

[57] ABSTRACT

A method and reagents are disclosed for minimizing interference from halide ions in ion-selective electrode analysis. A reagent consisting of a mixture of a metal and a chelating agent is introduced to the fluid sample being analyzed. This reagent forms soluble complexes with halide ions in the fluid sample, thus minimizing their effects.

7 Claims, No Drawings

ION SELECTIVE ELECTRODE ANALYSIS

FIELD OF INVENTION

This invention relates to the ion-selective electrode analysis of an analyte in a fluid sample and, more particularly, to a method and reagents for minimizing interference from halide ions in the fluid sample.

BACKGROUND OF THE INVENTION

The interference of bromide and iodide ions in the analyses by ion-selective electrodes of chloride ion in a fluid sample has been a long standing problem. These halide interferants have severely limited the use of ion-selective electrodes to perform an accurate analysis. Chemical similarity between chloride ions and bromide or iodide ions causes difficulty in the separation or elimination of these interferants from solution. To date, no convenient way has been found to reduce the interference of these halide ions.

Bromide and iodide ions are usually found in samples at a much lower concentration than the chloride ion. As such, these interferants do not usually pose a problem with most analyzing methods. However, this is not the case with an ion-selective electrode analysis of the chloride ion. In an ion-selective electrode analysis, these interferants, even at very low concentrations, will cause a significant distortion in the chloride ion response. This is due, in part, to the mechanism of the response, i.e., bromide and iodide ions disturb the sensitivity of the electrode and, also, to the fact that ion-selective electrodes measure ions logarithmically in accordance with the Nernst equation. Accordingly, the presence of such interferants will produce a measured chloride ion concentration much in excess of the actual concentration.

The several methods which are known to separate or eliminate the bromide and iodide ions from solution are not easy to accomplish. For example, it is possible that boiling the solution with nitric acid will remove the bromide and iodide ions. Also, it is possible that these interferants can be precipitated from solution by heavy metals such a Pb. Ion exchange columns can also be used to rid the fluid sample of bromide and iodide ions.

All of the above known separation methods are either time consuming or are unsatisfactory for other reasons. Therefore, there has been a long felt need to provide a simple and convenient way of minimizing the effects of these interferants upon the ion-selective electrode analysis of chloride ions in a fluid sample.

PRIOR ART

It has been shown that bromide and iodide ions may be quantitatively determined by spectrophotometric methods with the use of mercury(II)-ethylenediaminetetraacetic acid, and mercury(II)-cyclohexanediaminetetraacetic acid, as taught in the following articles: Ultraviolet Spectrophotometric Determination of Bromide and Iodide Ions with Mercury Ethylenediaminetetraacetate by Sumio Komatsu and Toshiaki Nomura (Shinshu Univ., Matsumoto, Japan), Nippon Kagaku Zasshi 88 (1), 63-6 (1967), (Japan) and Ultraviolet Spectrophotometric Determination of Iodide with Mercury(II) Cyclohexanediaminetetraacetate by Toshiaki Nomura (Shinshu Univ., Matsumoto, Japan), Nippon Kagaku Zasshi 88 (2), 199-202, (1967), (Japan).

While the above articles suggest complexing the metal chelates with the bromide and iodide ions for spectrophotometric analysis, there is no teaching that this technique is applicable to reduce the effects of halide ions as interferants in an analyte analysis. This is especially true when this analysis further involves the use of an ion-selective electrode as the measuring instrumentality.

SUMMARY OF THE INVENTION

The invention pertains to a method and reagents for minimizing the interfering effects of halide ions in the ion-selective electrode analysis of a fluid sample.

It has been discovered that the interfering effects of halide ions upon an ion-selective electrode can be substantially reduced in the presence of metal chelates, which form soluble complexes with the halide ions. In a chloride ion analysis, the ion-selective electrode will respond both to the chloride ions and the free bromide and iodide ions in solution, such that the complexing of the bromide and iodide ions reduces their interfering effects. Therefore, the inventive method introduces a reagent into the fluid sample to form soluble complexes with the halide interferants.

DETAILED DESCRIPTION

The following Table I illustrates the observed typical interferance of several concentrations of bromide and iodide ions upon a chloride ion analysis as performed by an ion-selective electrode. Column 1 (left-hand column) lists the interfering ion; column 2 states the particular ion concentration in the fluid sample; column 3 expresses the effect of the ion as a measurement of the chloride ion without the use of the complexing reagent(s); and column 4 shows the reduction of the interfering effect of the ion (expressed as a measurement of the chloride ion) with the introduction of the inventive metal chelating reagent(s). Columns 3 and 4 state a range of the measurement of the chloride ion concentration, or the exact measured concentration of the ions will depend upon the particular metal chelate that is introduced into the fluid sample.

Table I

| Inter-fering Ion | Concentration (mmol/l) | Interference Expressed as mmol/l Chloride | |
|---|---|---|---|
| | | without Metal-Chelate | with Metal-Chelate |
| Bromide | 1 | 30–100 | 0–5 |
| Bromide | 5 | 70–300 | 1–20 |
| Iodide | 1 | 10–30 | 0–3 |
| Iodide | 10 | 40–100 | 9–20 |

The metals and chelating agents of the inventive reagent mixture introduced into the sample, which have been found to be sufficiently effective in reducing the aforementioned interferant effects, are listed in Table II below:

TABLE II

1. Metals
   Mercury
   Silver
   Lead
   Bismuth
   Copper
   Cadmium
2. Chelating Agents
   Ethylenediamine
   n-butylamine
   Triethylenetetramine
   Ethylenediaminetetraacetic acid TABLE II-continued Cyclohexanediaminetetraacetic acid
Ethyleneglycol-bis-(2-aminoethyl ether) tetraacetic acid
Nitrilotriacetic acid While any combination of the above metals and chelating agents have been observed to provide an effective reagent, it must be realized that this is only a partial listing of the substances which may be used in the invention; the sake of brevity preventing a more comprehensive listing.

A preferred metal and chelating agent mixture for the inventive reagent in a chloride ion analysis has been observed to be the mercury(II)-ethylenediaminetetraacetic acid combination.

A preferred buffer reagent and pH has been observed to be the phosphate buffer at pH 6.5.

With all of the aforementioned reagent mixtures, it also has been found useful to add a buffer to the fluid sample to adjust the pH of the solution. The reason for this is threefold: (a) most clinical fluid samples are adjusted to a particular pH for standardizing their testing; (b) in flow systems, such a pH adjustment reduced liquid junction problems; and (c) the effectiveness of a particular metal chelating agent combination depends upon the pH and the type of buffer reagent used.

Having thus described my invention, what is desired to be protected by Letters Patent is presented in the following appended claims:

What is claimed is:

1. A method of minimizing the effects of halide interferants in the analysis of an analyte in a fluid sample by an ion-selective electrode, comprising the steps of: (a) introducing a reagent into said fluid sample to form soluble complexes with said halide interferants in said fluid sample; and (b) analyzing said fluid sample for said analyte by means of said ion-selective electrode.

2. The method of claim 1, wherein said reagent comprises a mixture of a metal and a chelating agent, and further wherein said metal is selected from a group consisting of: mercury, silver, lead, bismuth, copper and cadmium.

3. The method of claim 1, wherein said reagent comprises a mixture of a metal and a chelating agent, and further wherein said chelating agent is selected from a group consisting of: ethylenediamine, n-butylamine, triethylenetetramine, ethylenediaminetetraacetic acid, cyclohexanediaminetetraacetic acid, ethyleneglycol-bis-(2-aminoethyl ether) tetraacetic acid and nitrilotriacetic acid.

4. The method of claim 1, wherein the analysis of said fluid sample is for chloride ion, and the halide interferants are bromide and iodide ions.

5. A reagent for use in combination with an ion-selective electrode for minimizing the effects of halide interferants in an analysis of a fluid sample by said ion-selective electrode, said reagent consisting of: a mixture comprising a metal and a chelating agent, said metal and chelating agent forming soluble complexes with said halide interferants in said fluid sample, whereby the effects of said halide interferants upon the analysis of said ion-selective electrode is minimized.

6. The reagent of the combination of claim 5, wherein said metal is selected from a group consisting of: mercury, silver, lead, bismuth, copper and cadmium.

7. The reagent of the combination of claim 5, wherein said chelating agent is selected from a group consisting of: ethylenediamine, n-butylamine, triethylenetetramine, ethylenediaminetetraacetic acid, cyclohexanediaminetetraacetic acid, ethyleneglycol-bis-(2-aminoethyl ether) tetraacetic acid, and nitrilotriacetic acid.

* * * * *